(12) United States Patent
Botman et al.

(10) Patent No.: US 9,044,781 B2
(45) Date of Patent: Jun. 2, 2015

(54) MICROFLUIDICS DELIVERY SYSTEMS

(71) Applicant: FEI Company, Hillsboro, OR (US)

(72) Inventors: Aurélien Philippe Jean Maclou Botman, Portland, OR (US); Steven Randolph, Portland, OR (US); Mark W. Utlaut, Scappoose, OR (US)

(73) Assignee: FEI COMPANY, Hillsboro, OR (US)

( * ) Notice: Subject to any disclaimer, the term of this patent is extended or adjusted under 35 U.S.C. 154(b) by 113 days.

(21) Appl. No.: 13/693,938

(22) Filed: Dec. 4, 2012

(65) Prior Publication Data

US 2014/0151335 A1    Jun. 5, 2014

(51) Int. Cl.
| | | |
|---|---|---|
| *B05D 1/26* | (2006.01) | |
| *C25D 5/02* | (2006.01) | |
| *C25F 3/14* | (2006.01) | |
| *G01N 23/225* | (2006.01) | |

(52) U.S. Cl.
CPC *B05D 1/26* (2013.01); *C25D 5/024* (2013.01); *C25F 3/14* (2013.01); *G01N 23/225* (2013.01)

(58) Field of Classification Search
USPC ........................................................ 250/492.2
See application file for complete search history.

(56) References Cited

U.S. PATENT DOCUMENTS

| | | | |
|---|---|---|---|
| 4,876,112 A | 10/1989 | Kaito et al. | |
| 5,104,684 A | 4/1992 | Tao et al. | |
| 6,348,295 B1 | 2/2002 | Griffith et al. | |
| 6,633,381 B2 | 10/2003 | Uhl | |
| 7,317,515 B2 | 1/2008 | Buijsse et al. | |
| 7,674,706 B2 | 3/2010 | Gu et al. | |
| 7,977,631 B2 | 7/2011 | Mulders et al. | |
| 8,163,641 B2 | 4/2012 | Gu et al. | |
| 8,319,181 B2 | 11/2012 | Parker et al. | |
| 2006/0056904 A1* | 3/2006 | Haselton et al. | 401/198 |
| 2007/0151989 A1 | 7/2007 | Espinosa et al. | |
| 2011/0226819 A1 | 9/2011 | Mulders et al. | |
| 2012/0248460 A1 | 10/2012 | Abraham et al. | |
| 2013/0068611 A1* | 3/2013 | Botman et al. | 204/192.11 |

FOREIGN PATENT DOCUMENTS

| | | |
|---|---|---|
| EP | 2481828 | 8/2012 |
| WO | 2012038484 | 3/2012 |

OTHER PUBLICATIONS

Donnermeyer, Achim, 'Scanning Ion-Conductance Microscopy,' Aug. 16, 2007, Bieldefeld University.
Suryavanshi, Abhijit, et al., 'Probe-based electrochemical fabrication of freestanding Cu nanowire array,' Applied Physics Letters, Feb. 21, 2006, 3 pgs, vol. 88.

* cited by examiner

*Primary Examiner* — Phillip A Johnston
(74) *Attorney, Agent, or Firm* — Scheinberg & Associates, PC.; Michael O. Scheinberg

(57) ABSTRACT

Methods of dispensing a small amount of liquid onto a work piece includes in some embodiments known providing a microscopic channel for the liquid to flow from the nanodispenser. In some embodiments, dispensing the liquid includes dispensing the liquid using a nanodispenser have at least one slit extending to the tip. Some methods include controlling the rate of evaporation or the rate of liquid flow to establish an equilibrium producing a bubble of a desired size.

11 Claims, 14 Drawing Sheets

MICROFLUIDICS DELIVERY SYSTEMS

TECHNICAL FIELD OF THE INVENTION

The present invention relates to the use of microfluidics for charged particle beam systems.

BACKGROUND OF THE INVENTION

Microscopic processing often requires a small quantity of a compound to be provided at a precise location on a work piece. For example, vapor phase precursor molecules directed to a region of a work piece dissociate in the presence of a focused beam, such as a charged particle beam or a laser beam, to deposit material or to etch a work piece in a precise pattern. Stains or markers applied to a region of interest on a work piece surface may increase the contrast of structures in a biological system for imaging with an electron or optical microscope. An electrolyte applied to the surface of the work piece may be used for local electrochemical deposition or etching of a material. Reactants may combine in a microscopic reactor on a work piece to produce a desired product or to test for the presence of a substance.

Charged particle beams, such as focused ion beams or electron beams, and laser beams are often used with chemical compounds to process a work piece. For example, beams can be used to deposit material by beam-induced deposition, also known as "direct-write deposition." One method of direct-write deposition uses electron beam, ion beam, or laser beam-stimulated chemical vapor deposition, in which a precursor species dissociates due to the effects of the beam. Part of the dissociated molecule is deposited onto the substrate, and part of the dissociated molecule forms volatile by-products, which eventually releases from the work piece surface. The precursor can be, for example, a vapor that contains an organometallic material that includes a metal to be deposited. The metal is essentially deposited only in the area impacted by the beam, so the shape of the deposited metal can be precisely controlled with resolution close to that of the beam. The precursor is typically delivered to the work piece surface as a vapor using a needle that directs the precursor gas to the vicinity of the work piece where the beam impacts. An ion beam-assisted deposition process is described, for example, in U.S. Pat. No. 4,876,112 to Kaito et al. for a "Process for Forming Metallic Patterned Film" and U.S. Pat. No. 5,104,684 to Tao et al. for "Ion Beam-Induced Deposition of Metals."

Beam-induced processes can also be used to precisely etch a work piece, with the beam inducing a reaction between a precursor compound and a material on the work piece to form a volatile compound that leaves the surface. Because charged particle beams can be focused to a spot smaller than one tenth of a micron, charged particle beam processes provide for high-resolution fabrication, alteration, and imaging of microscopic structures. Charged particle beams operate in a vacuum, while lasers can operate either in atmosphere or in a vacuum.

Charged particle beams can also be used to form images and to study the properties of microscopic structures, for example, in transmission electron microscopy, scanning electron microscopy, scanning ion microscopy, energy dispersive electron spectroscopy, and Auger electron spectroscopy. Delivering compounds, such as stains and markers, to a precise location on a work piece can be useful in imaging and metrology. Markers may include heavy elements that provide improved contrast in electron beam images. Recent advances in super-resolution optical microscopy provide high-resolution images of biological structures, often in conjunction with markers, such as fluorescent proteins. An example of the use of a substance to enhance imaging of a work piece is shown in U.S. Pat. No. 7,977,631 to Mulders et al. for "Method for obtaining images from slices of specimen," which describes the use of staining with charged particle beam processing and imaging. In Mulders, a gas-phase stain is delivered to a freshly exposed surface of the work piece.

Processing micrometer and nanometer scale structures is required in many fields including biological sciences, microelectromechanical systems (MEMS) and semiconductor manufacturing. For example, semiconductor devices such as microprocessors can be made up of millions of transistors, each interconnected by thin metallic lines branching on several levels and electrically isolated from each other by layers of insulating materials. Biological sensors may include microscopic regions of biological material that detect an analytic, transducers and electronics that provide an interpretable detectable signal.

One application of beam processing is device editing—the process of modifying a device during its development without having to remanufacture the whole circuit. Device editing provides tremendous economic benefits by reducing both processing costs and development cycle times. Direct-write deposition and precise etching allows an engineer to test variations of the device without undertaking the lengthy process of modifying photolithography masks and fabricating a new circuit from scratch.

It is often difficult to obtain high purity materials using direct-write deposition, primarily due to the incorporation into the deposit of other components of the precursor molecules or the elements from the incident ion beam, such as gallium ions. This lack of control of composition, material purity, or internal structure often leads to undesirable properties in the deposited material. Tungsten and platinum deposited by focused ion beam (FIB)-induced deposition typically have resistivities greater than about 150 micro ohm centimeters ($\mu\Omega$-cm). Recently-introduced FIB copper depositions have resistivities of 30-50 $\mu\Omega$-cm. This is significantly higher than the resistivity of pure copper, which is less than 5 $\mu\Omega$-cm.

U.S. Pat. No. 7,674,706 to Gu et al. for "System for Modifying Structures Using Localized Charge Transfer Mechanism to Remove or Deposit Material" ("Gu") describes local electrochemical processing. The process of Gu provides improves purity and lower resistivity compared to ion beam-induced deposition. Gu deposits a localized drop of electrolyte on a portion of an integrated circuit and depositing or etching using an electric current flowing from a probe contacting the drop, through the electrolyte and then through the substrate. In one embodiment, the probe contacting the drop is replaced by using a charged particle beam to supply current, with the circuit being completed through the substrate.

Charged particle beam-induced deposition has been limited by the availability of vapor phase precursors with requisite properties, that is, high residency time (stickiness) on the surface, lack of spontaneous decomposition, and decomposition in the presence of the beam to deposit the desired material and form a volatile byproduct. When suitable deposition precursors do exist for a particular material, the deposition rates are often limited by gas depletion effects and other factors. The precursor molecules typically cause a substantial increase in the pressure in the vacuum chamber, which can scatter the beam, and most of the precursor molecules are removed by the vacuum pump without reacting, thereby wasting the precursor, which is often a hazardous substance.

FIG. 1 shows an apparatus for localized electrochemical deposition of conductors using a micro or nano pipette in close proximity to a conductive surface. Such a method is described in Suryavanshi et al. in "Probe-based electrochemical fabrication of freestanding Cu nanowire array," Applied Physics Letters 88, 083103 (2006) ("Suryavanshi"). A glass pipette 102 holds an electrolyte solution 104, such as 0.05 M $CuSO_4$. A power supply 106 provides current for the electrochemical reaction, with an electric circuit being formed between a copper electrode 108 and a conductive substrate 110. The process is typically carried out in atmosphere under the observation of an optical microscope. A device that moves about a surface writing a pattern is referred to as a "nano pen."

SUMMARY OF THE INVENTION

It is an object of the invention, therefore, to provide a method and apparatus for supplying small amounts of fluid for processing, particularly in a vacuum system.

Embodiments of the invention provide methods and apparatuses for dispensing a small amount of fluid. Some embodiments provide a method for controlling the flow of a liquid into an evacuated chamber. In some embodiments, a channel provides use of a nanocapillary having one or more slits in the end as a fluid dispenser. In some embodiments, slits in the tip of a nanodispenser provide improved flow of liquid from the nanodispenser.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF PREFERRED EMBODIMENTS

Figure 1:
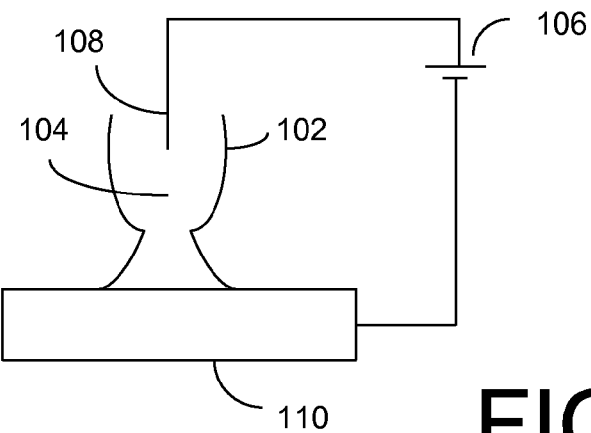
FIG. 1 shows a prior art electrochemical writing instrument.

Embodiments of the invention supply a small amount of liquid onto a work piece surface for micro or nanoprocessing. Some embodiments can dispense a precise amount of liquid and deliver the liquid to a precise location on the work piece. Some embodiments are especially useful in a vacuum chamber, such as a vacuum chamber of a charged particle beam system. Some embodiments are also useful outside of a vacuum chamber.

A "nanodispenser," as used herein, comprises a device that dispenses small quantities of liquid upon a substrate. Nanodispensers can comprise, for example, nanocapillaries, nanosyringes, nanopipettes, etc. A nanodispenser can move relative to the work piece dispensing liquid, or the nanodispenser can dispense from a fixed position.

The rate at which liquid is dispensed from the nanodispensers depends on the application. The apparent bubble size is a function of the dynamic equilibrium between evaporation of the fluid from the bubble into vacuum, and supply of liquid into the bubble from the nanodispenser. As such, while relevant, the rate of flow of liquid out of the nanodispenser is difficult to quantify. Instead the bubble size is quantified and this metric is more relevant for applications. The bubble size is typically less than 50 µm, more preferably less than 10 µm, and most preferably less than 2 µm.

The liquid can be used in various processes, including charged particle beam processes, laser processes, electrochemical processes, enhancing microscopy of biological samples, and chemical nano or microreactors. Some of the processes in which the invention can be used are described in U.S. Pat. No. 6,236,587, of Botman et al, filed Sep. 9, 2011, for "Localized In-Vacuum Modification of Small Structures," ("Botman") which is hereby incorporated by reference. For example, the dispensed liquid can be an electrolyte, and an electric current through the electrolyte then electrochemically deposits material onto the surface or etches material from the surface.

Botman describes applications in which the liquid can be used to deposit metals that are substantially pure. Because the metals are pure, they can have resistivities that are 40 or more times lower than the resistivities of existing FIB-induced deposition of tungsten and platinum materials, and ten times lower than the resistivity of FIB-induced deposition of copper conductive materials. The resistivities are comparable to those of pure metals, for example less than 100 μΩ-cm, more preferably less than 50 μΩ-cm, even more preferably less than 25 μΩ-cm or less than 10 μΩ-cm, and most preferably less than 5 μΩ-cm. The deposited metals can be greater than 90% (atomic percent) pure, more preferably greater than 95% pure, and most preferably greater than 99% pure. Alloys could be deposited using solutions containing multiple metal ion species.

In some embodiments, the nanodispenser operates in the sample vacuum chamber of a charged particle beam system, such as a scanning electron microscope (SEM), focused ion beam (FIB), or an environmental SEM. Environmental SEMs typically operate with the sample in a chamber at a pressure between 0.07 and 50 Torr, which is much higher than the pressures in the vacuum chamber of a conventional SEM or FIB, typically less than $10^{-5}$ mbar. A liquid used in some embodiments of the invention will raise the pressure in the vacuum chamber, but the higher operating pressure can still be within the operating limits of an SEM, FIB or environmental SEM. In some embodiments, the sample and/or the nanodispenser may be cooled to reduce the vapor pressure and maintain working pressures in the SEM, FIB or environmental SEM sample chamber within the operating limits.

When the process is used in an environmental SEM, the SEM image can be used to position and direct the nanodispenser, manually or automatically, for forming a deposition pattern and for monitoring the process with great precision. The high resolution of the SEM facilitates an automated process, in which the position of the nanodispenser and the material being deposited or etched is observed and interpreted using pattern recognition software. The position of the nanodispenser and the state of the process, such as the geometry of the deposit or etch, are measured and fed back to the process controller to correct the process in real time, that is, while it is being performed, providing a closed loop feedback system. Such embodiments overcome a limitation of prior art systems, such as that of Suryavanshi, in which the accuracy of the placement of the nanodispenser is limited by the resolution of an optical microscope.

As described in Botman, operating in a vacuum chamber allows use of a charged particle beam, which can induce reactions, such as decomposition of a precursor and charge transfer reactions, in which the charged particle beam can be used as a virtual electrode. Prior art electrochemical, direct-write processes for directly depositing a material onto a surface are not compatible with insulating surfaces as the insulating surface prevents the electrochemical circuit from being formed. Embodiments of the present invention, using a charged particle beam itself as a virtual cathode and a conductive nanodispenser to locally apply the electrolyte, allow deposition on an insulating surface. An electrode for the electrochemical reaction can also be supplied by existing conductors on the work piece or by conductors deposited by a beam-induced deposition or implantation.

In some embodiments, the fluid is dispensed from the nano-dispenser using capillary forces only, as opposed to hydrostatic pressure. Hydrostatic flow of fluid for localized delivery requires a large diameter at the interface of fluid to vacuum, resulting in large uncontrollable amounts of liquid being delivered. The electrolyte capillary bubble in these types of applications typically has a diameter between 30 μm and 50 μm in low vacuums using pressure driven flows. A smaller diameter of, e.g., less than 10 μm is preferred for more precise deposition. When the diameter of a capillary is relatively large, liquid can be easily extracted by applying a pressure differential across the liquid in the capillary, that is, pressure is applied at the back end to push the liquid out of the capillary tip. As the diameter of the tip gets very small, an impractically large hydrostatic pressure would be required to force out the liquid, but the liquid can be extracted using capillary action by contacting the end of the nanocapillary with the substrate surface. Capillary action is caused by a combination of surface tension and adhesion of the liquid to a solid.

The diameter of the nanodispenser at which capillary action dominates over hydrostatic pressure for extracting liquid depends on the surface tension of the liquid, on the adhesion between the liquid and the material of which the nanodispenser is composed, and on the adhesion between the liquid and the material of which the substrate is composed. When the nanodispenser is composed of borosilicate glass, the liquid is ultrapure water, and the substrate surface is silicon, the diameter of the nanodispenser is preferably less than 20 μm, more preferably less than 10 μm, and most preferably less than 5 μm.

Some embodiments use capillary forces to define fluid flow in a controlled manner, supply the fluid at a precise location on the surface, and deliver adequately small amounts of liquid to the surface. This enables the fluid to flow in a defined and controlled manner upon contact of the nanodispenser to the surface/substrate. Providing fluid flow via only capillary flow results in: (1) directed flow only upon contact of the nanocapillary to the surface; (2) smaller amounts of fluid can be delivered; and (3) fluid can be supplied at a precise location on the surface to support high resolution processing.

Direct-write processes have been limited to directing the charged particle beam toward the electrolyte solution bubble or just on the periphery of the bubble, as delivered by the nanodispenser. This has made it difficult to alter microstructures in electrically isolated areas. Botman describes that deposition can be performed away from the electrolyte solution itself due to a very thin layer of solution that diffuses away from the bubble. The thin coating of liquid evaporates rapidly and can coat areas that are not involved in the process, which may be undesirable. Using flow channels as described herein keeps the liquid from contaminating areas of the work piece surface that are not involved in the processing.

Because the electrolyte is applied locally to plate a small area, no electroplating bath is needed. Most of the work piece remains dry. The specific plating solution used will depend on the application; many electroplating solutions are known in the art. For example, one suitable solution comprises ENTHONE ViaForm® Make-up LA, to which is added 5 ml/L of ENTHONE ViaForm® Accelerator and 2 ml/L ENTHONE ViaForm® Suppressor. The ENTHONE ViaForm® solutions are available from Enthone, Inc., West Haven, Conn. Metals such as Cu, W, Au, Pt, Pd, Ag, Ni, Cr, Al, Ta, Zn, Fe, Co, Re, etc., and alloys composed of these metals can also be written using the nanodispenser.

Figure 2:
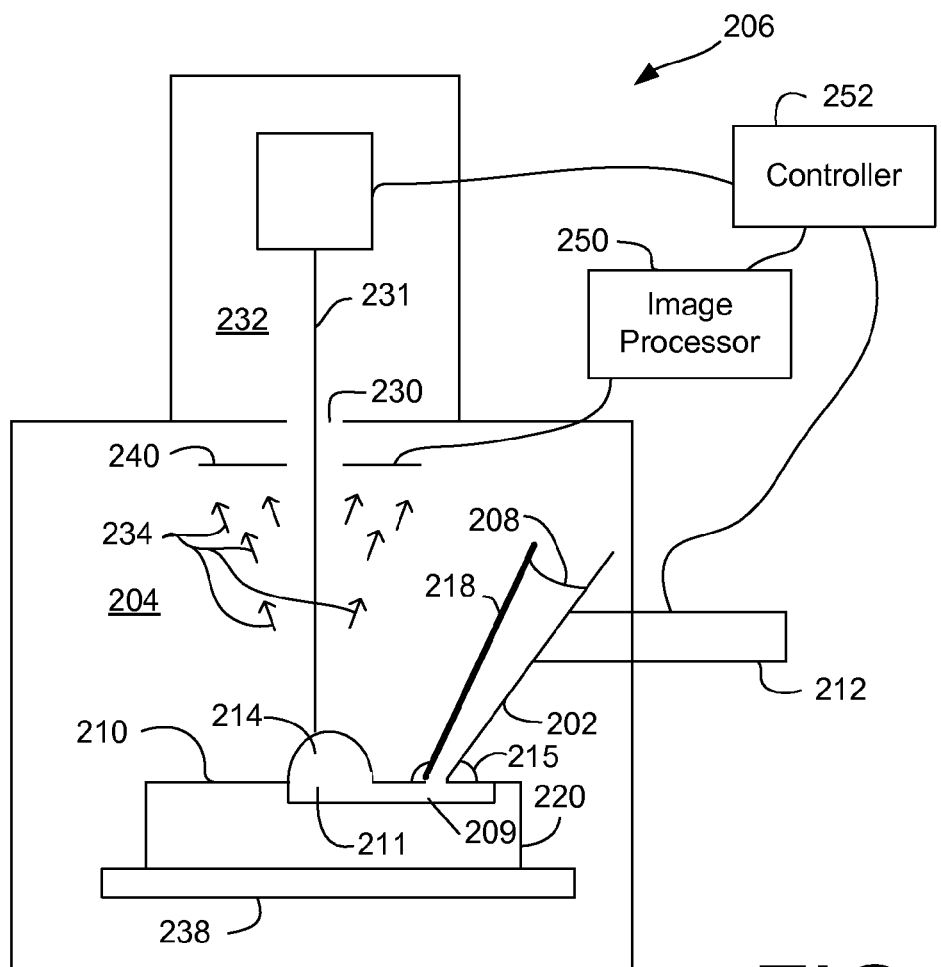
FIG. 2 shows a system for dispensing a liquid at a location other than the location of use.

FIG. 2 shows an embodiment of the invention in which a nanocapillary 202 is used to provide a liquid precursor for charged particle beam deposition or etching within sample vacuum chamber 204 of a charged particle beam system, such as a focused ion beam system or an environmental scanning electron microscope 206. Nanocapillary 202 can deliver a liquid, such as a liquid precursor solution 208 to a channel 209 in work piece surface 210. Liquid precursors can include, for example, $CuSO_4$ for beam-assisted deposition or beam-assisted etching, and KCN or $FeCl_3$ for wet etching. Channel 209 leads to an accumulation point 211, where the liquid is accumulated for processing by the charged particle or in, some embodiments, by a laser beam. The liquid precursor forms a bubble 214 on the surface 210. Another bubble 215 may form at the point of around the contact point of the nanocapillary 202 and the surface 210. The nanocapillary may contact the work piece surface within the channel or sufficiently close to the channel to allow the liquid to flow into the channel. The nanocapillary may be positioned slightly above the surface, such that a liquid meniscus, but not the nanocapillary itself, contacts the surface. The surface may be hydrophilic or hydrophobic, although it is preferably hydrophilic. Nanocapillary 202 is attached to a micromanipulator 212 that preferably provides motion in three axes and rotation along the capillary axis. In some embodiments, as described in Botman, a modified gas injection system, which is a common accessory in charged particle beam systems, can be used as the micromanipulator.

A pressure limiting aperture 230 maintains a pressure differential between an electron optical column vacuum chamber 232 and the sample vacuum chamber 204 to reduce dispersion of the primary electron beam 231 by gas molecules. Thus, evaporation of the liquid precursor 208 increases pressure in the sample vacuum chamber 204, but much less so in the electron optical column vacuum chamber 232. The sample in some embodiments is preferably cooled or heated, for example, by a thermoelectric cooler 238 or heater (not shown), to modify the relative humidity at the substrate as compared to the bulk of the chamber. In some embodiments, the nanocapillary is also cooled or heated, for example, by a thermoelectric cooler or heater (not shown).

The processing can be observed by the environmental scanning electron microscope 206, in which electron beam 231 scans the region where material is being deposited and secondary electrons 234 are emitted upon impact of electron beam 231. The secondary electrons 234 are amplified by gas cascade amplification and detected by an electrode 240, forming an image whose brightness at each point corresponds to the current detected by the electrode 240. The image can be used to monitor and adjust the progress of the deposition or etching to provide real time feedback to an operator. The image can be used to position and guide the nanocapillary 202 during deposition or etch.

In some embodiments, the deposition or etch can be automated. An image processor 250 uses pattern recognition software to recognize the nanocapillary and the substrate around it. A controller 252 controls the movement of the nanocapillary through micromanipulator 212 in accordance with a predetermined pattern. The image from the electron microscope can provide real time position information for closed loop feedback so that the position of the nanocapillary 202 can be controlled to produce the desired pattern on the surface 210. The deposition or etch pattern can also be observed to adjust the deposition process, such as the speed of the nanocapillary or the pressure at which the nanocapillary contacts the surface.

As described above, the diameter is preferably sufficiently small so that the liquid is forced out of the nanocapillary by capillary action when the capillary or liquid is in contact with the surface, rather than through hydrostatic pressure, but not so small that thermodynamic self-cooling and subsequent freezing at the nanocapillary leads to clogging, as described further below.

Figure 3:
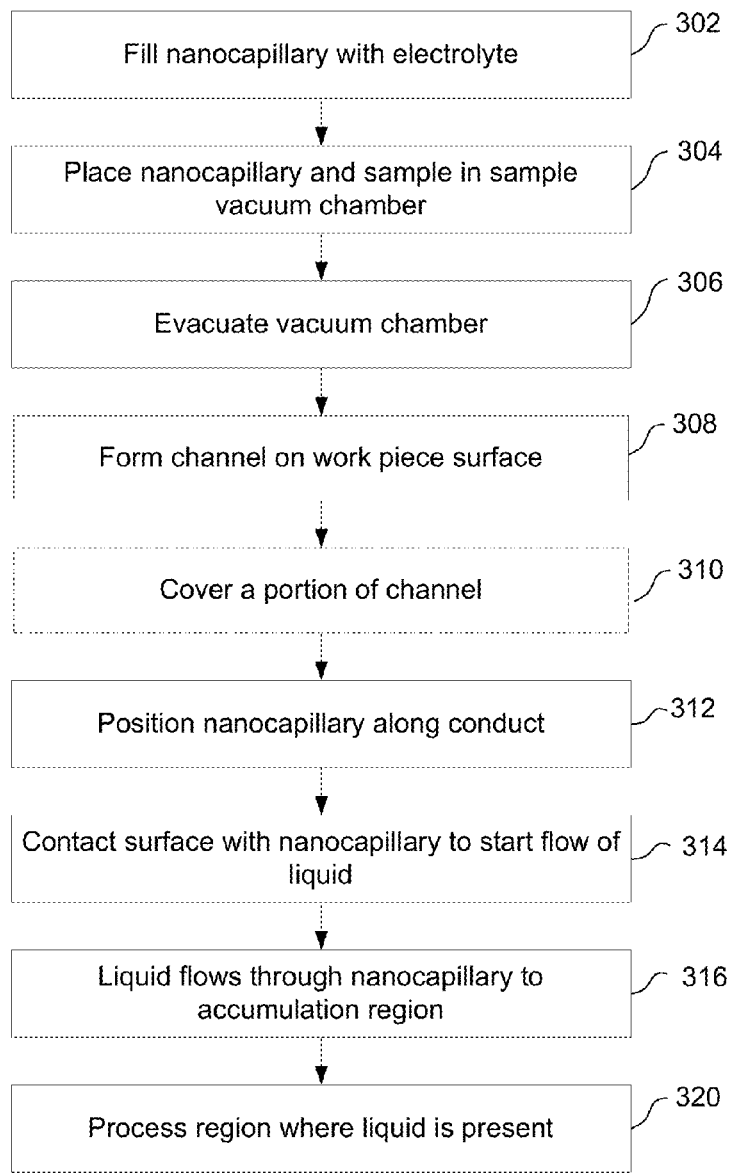
FIG. 3 is a flow chart showing a method of dispensing a small quantity of liquid at a location other than the location of use.

FIG. 3 is a flowchart showing the operation of the system of FIG. 2 in an embodiment of the invention. In step 302, the nanocapillary is filled with electrolyte as described, for example, in Botman. In step 304, the nanocapillary and the work piece are placed in a vacuum chamber of a focused ion beam system. The nanocapillary is preferably positioned in a micromanipulator so that it can be oriented, positioned, and moved. The sample is typically placed on a moveable three-axis stage. In step 306, the vacuum chamber is evacuated to produce a vacuum acceptable for a focused beam process, typically a pressure lower than $10^{-5}$ Torr ($1.3 \times 10^{-5}$ mbar) if operating in High Vacuum mode, or 0.07-50 Torr (0.09 mbar-65 mbar) if operating in Environmental mode.

When fluid is placed by touching a nanodispenser onto the work piece surface, it can be difficult to precisely control the exact position that the nanodispenser contacts the work piece and the exact amount of fluid that flows from the nanodispenser. Some embodiments use a channel on the work piece to conduct the liquid to a position or positions on the surface.

In step 308, a channel is formed in the work piece to direct the flow of fluid. The channel may be formed using any suitable process. For example, the channel may be formed using a focused ion beam, either with or without an etch-enhancing precursor gas. The channel may also be formed by electron beam-induced etching or by a laser. The laser may be, for example, an ultra-fast pulsed laser that forms the channel by ablation. Other types of lasers, such as slower pulsed lasers or continuous lasers, and other laser processes, such as photochemical etching or photothermal-induced etching, can also be used. Channels can also be formed using photolithography.

Figure 4:
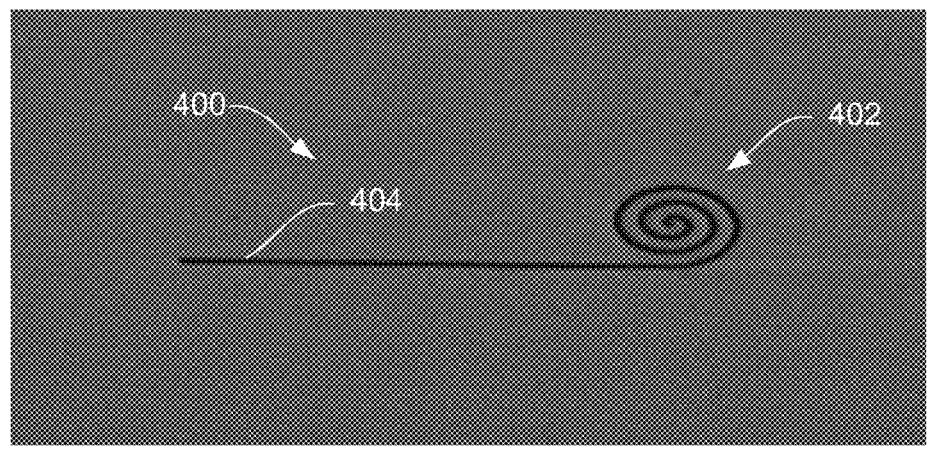
FIG. 4 shows a channel for conducting liquid and an accumulation point for the liquid, the channel and accumulation point having been formed by a focused ion beam.

FIG. 4 shows an example of a channel structure 400 that was milled using a focused ion beam. The sample includes an accumulation region 402 and a transport channel 404. While a spiral accumulation region is shown, any shape can be used. The accumulation region preferably includes channels that are sufficiently close together that the liquid in the adjacent channels will contact and join together. The channel allows the liquid to be delivered to a precise location, even though the location at which the nanocapillary contacts the substrate may not be precisely determined. Multiple channels can be used to cause small quantities of liquids to mix for performing nanochemistry reactions. That is, multiple nanodispersers can dispense small amounts of liquid to different points, and the liquid can follow the channels to a common working area, where the liquids mix together and react. The liquid transfers rapidly, for example, less than 10 seconds to move tens of microns. In one embodiment, channels of length greater than 100 microns have been demonstrated. Some embodiments do not require an accumulation region. The transport channel itself may be where the fluid is desired to provide the liquid and where the processing occurs.

The dimension across the top of the channel is preferably between 0.1 µm and 30 µm, more preferably between 0.1 µm and 10 µm, and more preferably between 0.1 µm and 5 µm. The channel depth is preferably between 0.1 µm and 20 more preferably between 0.1 µm and 10 and more preferably between 0.1 µm and 5 µm. The channel length is preferably between 0.1 µm and 500 µm, and more preferably between 0.1 um and 200 um. Channels may be straight or curved or contain segments meeting at an angle. Multiple channels may combine into fewer channels. Channels may branch out into a larger number of channels. Channels may optionally start, end, and/or traverse through larger fluid accumulation areas. Channels may pass alongside each other with a proximity designed to let the transported fluid either interact or not interact.

Figure 5:
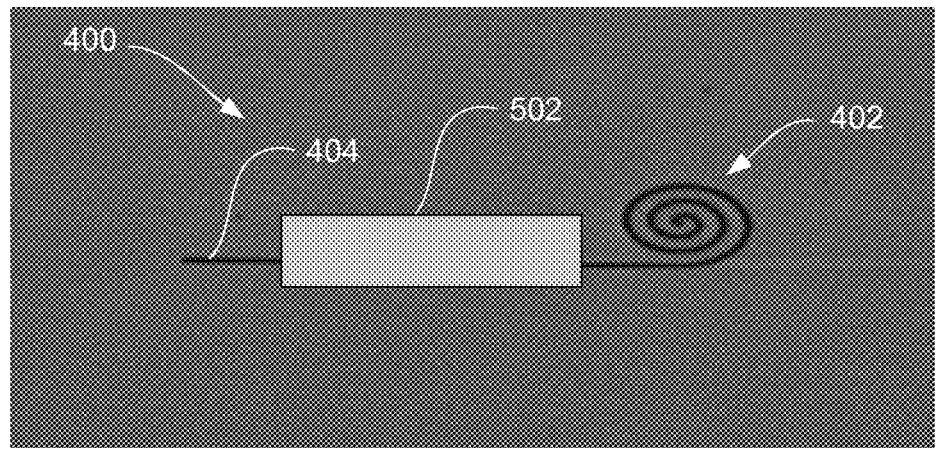
FIG. 5 shows the channel of FIG. 4 with a portion of the channel covered to prevent evaporation of the liquid.

In optional step 310, a portion of channel 404 is covered to reduce evaporation. FIG. 5 shows a cover 502 over a portion of channel 404. The cover can be provided, for example, by charged particle beam-induced deposition using a precursor gas. The cover can be formed, for example, by building up walls on both sides of the conduit and then extending the walls gradually toward the center of the channel to form the cover without filling the channel. A portion of the channel can also be covered by placing a preformed cover, such as a glass or silicon cover, into position over the channel using, for example, a micromanipulator.

Figure 6:
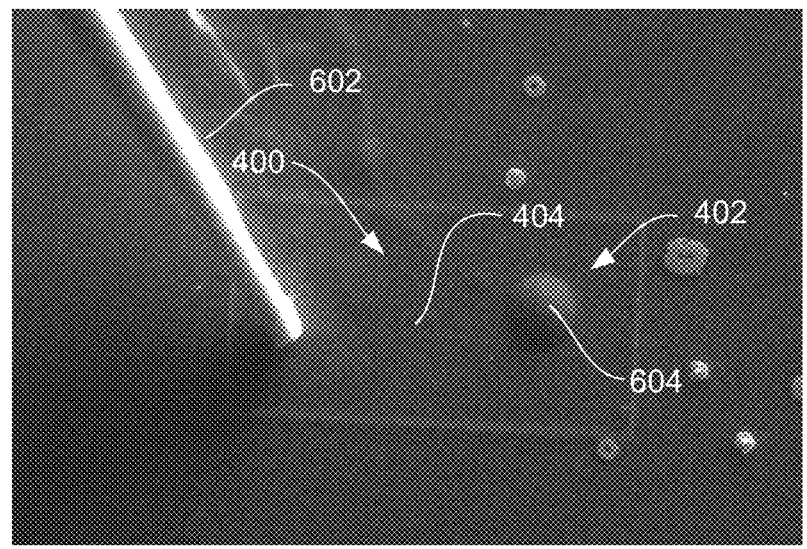
FIG. 6 shows the channel of FIG. 4 having a liquid dispensed therein.

In step 312, the nanocapillary is positioned somewhere along the transport channel 404. The positioning can be facilitated by observing the nanocapillary and the sample using an optical microscope, a scanning electron microscope, or a scanning ion microscope. In step 314, the nanocapillary is moved against the surface of the sample, somewhere along the channel and the liquid begins to flow. Positioning the nanocapillary anywhere along the transport channel 404 is typically easier than positioning the nanocapillary at a precise point. Moreover, using transport channel 404 to transport the liquid away from the point where the nanocapillary contacts the surface may facilitate processing, by eliminating interference by the nanocapillary, which can obstruct a processing beam. In step 316, the liquid flows through the conduit region to the accumulation region. The surface tension draws the liquid into and through the channel. FIG. 6 is a photomicrograph showing a nanocapillary 602 contacting the work piece surface along channel 404 and shows liquid 604 accumulated at accumulation point 402. In some embodiments there are multiple accumulation regions. In some embodiments, there are no accumulation regions, and the processing is performed on the fluid in the channels.

In step 320, the regions where the fluid is present are processed. Processing may include, for example, directing a charged particle beam or laser beam at a region of the liquid. For example, the liquid may be a precursor material that decomposes in the presence of a charged particle beam or laser beam to deposit material onto the work piece. The liquid may be a precursor material that reacts in the presence of a charged particle beam or laser beam to etch the work piece surface, forming volatile compounds that are removed from the vacuum chamber by a vacuum pump. The liquid may be a stain or a reactive liquid that reacts with material on the work piece. The liquid may be an electrolyte that is used to electrochemically deposit material onto the surface or to etch material from the surface, as described in Botman. When the liquid is used as an electrolyte in an electrochemical reaction, one electrode of the electrochemical circuit can be provided by a conductor attached to the nanocapillary, such as a conductive coating or a thin wire within the nanocapillary. The other electrode of the electrochemical circuit can be provided by a conductor pre-existing or deposited onto the work piece, or a charged particle beam can be used as a virtual electrode.

Figure 7:
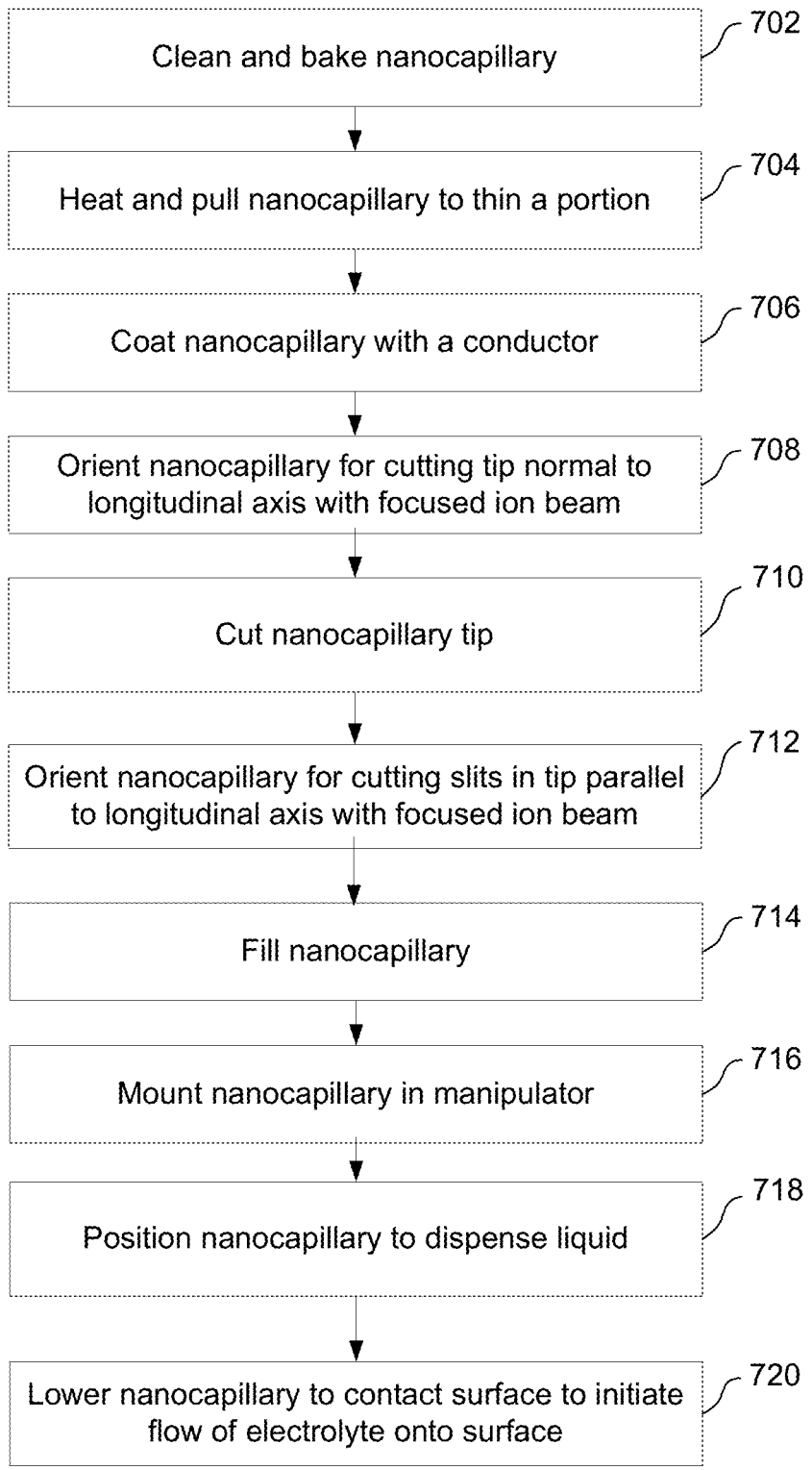
FIG. 7 is a flow chart showing a procedure for preparing the nanocapillary.

FIG. 7 is a flowchart showing one method of preparing a nanocapillary for use with the present invention. The starting material can be, for example, a borosilicate tube having an inner diameter of 0.5 mm and having an internal filament to assist filling. Such nano-capillaries are commercially available from Sutter Instruments Company, Novato, Calif. In step 702, the nanocapillary is cleaned and baked. In step 704, the nanocapillary is heated and pressure is applied along the long axis of the tube to create small tips, preferably less than 100 nm, at the end of the nanocapillary. This step is referred to as "pulling," which can be performed using commercially available "pullers," also available from Sutter Instruments Company.

Figure 8:
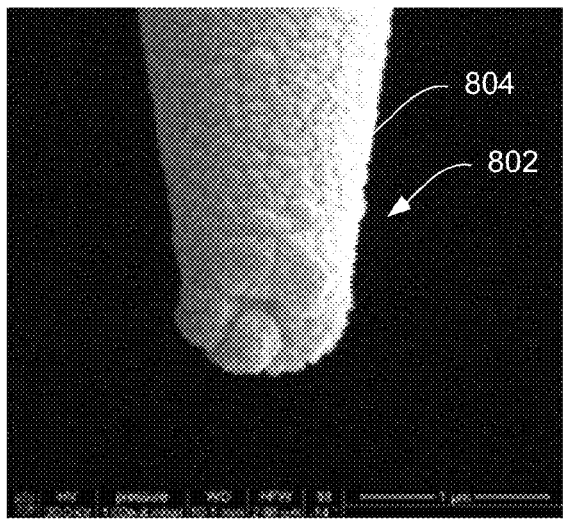
FIG. 8 shows a nanocapillary after depositing a conductor on the outer wall.

In step 706, the nanocapillary is optionally coated with a conductor. For example, the nanocapillary can be sputter-coated with gold. Before coating, the end of the nanocapillary that was not narrowed is preferably covered, for example, with aluminum foil, to prevent sputtered material from reducing the inner diameter of the tube at the end that will be filled. A specific procedure that has worked efficiently is to coat the nanocapillary for eight minutes on each of two sides at 15 mA DC magnetron sputter current. Another specific procedure that has worked efficiently is to coat for four minutes on each side with Cu at 15 mA power followed by six minutes on each side with Au at 15 mA; in this procedure the Cu serves as an adhesion layer for the Au coating. FIG. 8 shows the tip of nanocapillary 802 after coating with a conductive coating 804.

Figure 9:
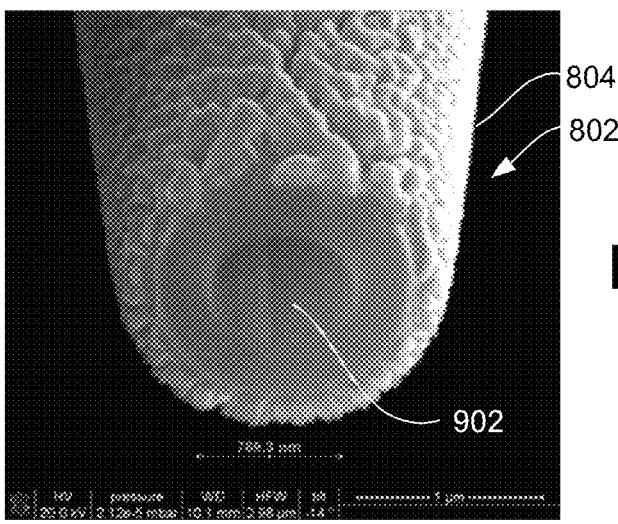
FIG. 9 shows the nanocapillary of FIG. 8 with the end cut off to open a hole
Figure 10:
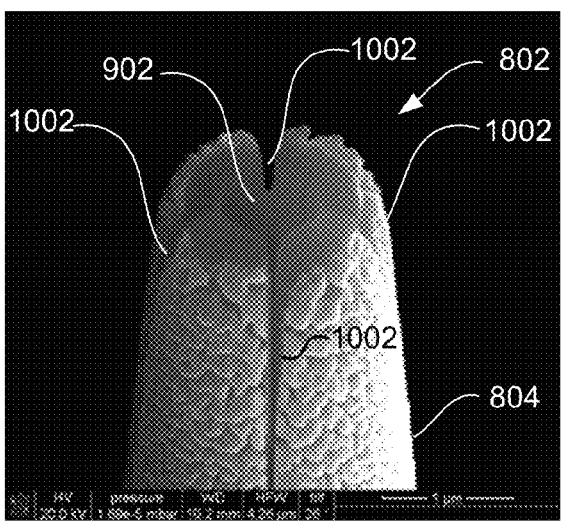
FIG. 10 shows the nanocapillary of FIG. 9 with slits cut in the tip.

In step 708, the nanocapillary tip is oriented for cutting the tip perpendicular to the long axis of the nanocapillary using a focused ion beam. In 710, the tip is cut. FIG. 9 shows the nanocapillary after being cut to expose an opening 902 in the end of nanocapillary 802. In 712, the nanocapillary is reoriented so that slits 1002 parallel to the long axis of the nanocapillary are cut in the tip. FIG. 10 shows the slits 1002. The slits in the tip facilitate liquid flow from the nanocapillary. While four slits 1002 are shown, fewer or more slits could be used. Moreover, the slits do not need to extend all the way through the nanocapillary tube-grooves in the nanocapillary interior could also be used. The slits provide a more reliable flow than prior art nanocapillaries.

After the nanocapillary is formed, it is filled in step 714. As described above, some embodiments of the invention use a nanocapillary having a sufficiently small inner diameter that the electrolyte flows by capillary action rather than by hydrostatic pressure. The small diameter of the nanocapillary makes filling difficult because of the surface tension of the liquid filling. Reliable and reproducible capillary flow when the nanocapillary touches the substrate within a vacuum chamber depends on the geometry of the tip of the nanocapillary and adequate filling of the nanocapillary with electrolyte. A method of filing a nanocapillary is described in Botman and also described below.

In step 716, the nanocapillary is attached to the micromanipulator. Good electrical contact between the conductive coating on the nanocapillary and the metal of the micromanipulator can be provided by applying silver paint to the junction. The drying of the silver takes about 10-20 minutes, and two layers are typically applied. The nanocapillary is then ready for use. It is positioned for dispensing liquid in step 718 and then contacted to the work piece surface in step 720. The flow from the nanocapillary to the substrate or surface is primarily due to capillary forces, and as such, the tip of the nanocapillary contacts the substrate directly to induce a flow.

Figure 11:
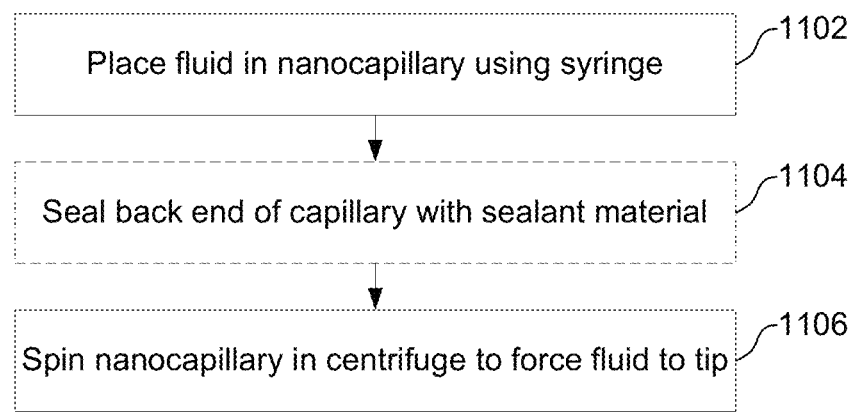
FIG. 11 is a flow chart showing a procedure for forming a nanocapillary.
Figure 12A:
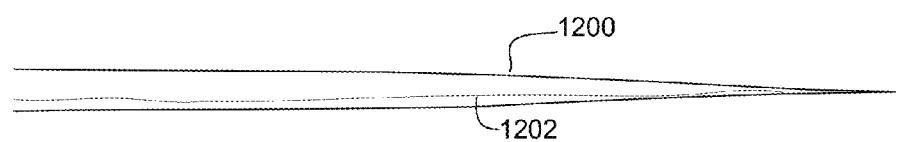
FIG. 12A-D shows a sequence of steps involved in filling the nanocapillary.
Figure 12B:
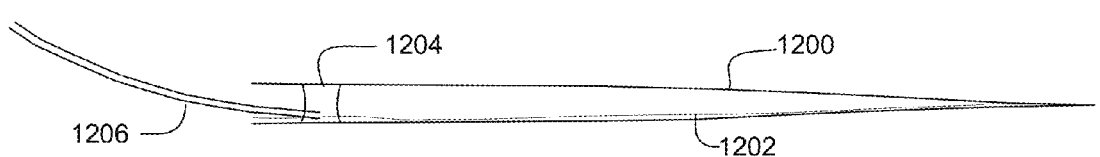
Figure 12C:
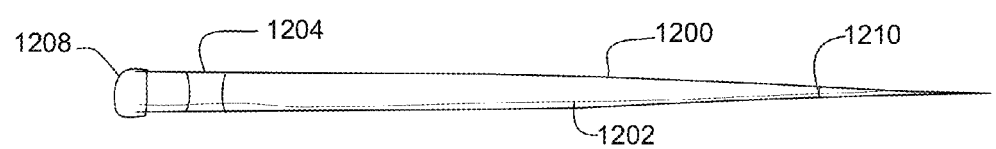

A method of filling the nanocapillary is described in Botman. FIG. 11 describes a method for filling a nanocapillary. FIG. 12 illustrates various steps of the process shown in FIG. 11. FIG. 12 is adapted in part from FIG. 4.3 from Donnermeyer, A. 2007. Thesis. Scanning Ion-Conductance Microscopy. Bielefeld (Germany): Bielefeld University. FIG. 12A shows a nanocapillary 1200, which includes an internal filament 1202 to facilitate filling. In step 1102, illustrated by FIG. 12B, a fluid 1204 is placed inside the nanocapillary by filling it from the backside using a microloader 1206. The microloader is a syringe with a tip capable of fitting in the backside of the nanocapillary, where the diameter is about 500 microns or less. Although the internal filament in the nanocapillary causes some fluid 1204 to travel to the tip as shown by meniscus 1210 in FIG. 12C, much of the fluid remains away from the tip because of the small diameter of the nanocapillary 1200. Optionally, in step 1104, the back end of the nanocapillary is sealed with vacuum compatible material 1208 to prevent the fluid inside the nanocapillary from evaporating into the vacuum from the back end of the nanocapillary. One such material is vacuum compatible wax. The wax used can be, for example, Apiezon Wax W. Mild heat (approximately 110° C.) can be used to melt the wax and provide a good vacuum-tight seal. The fluid is thus effectively sealed inside the nanocapillary.

Figure 12D:
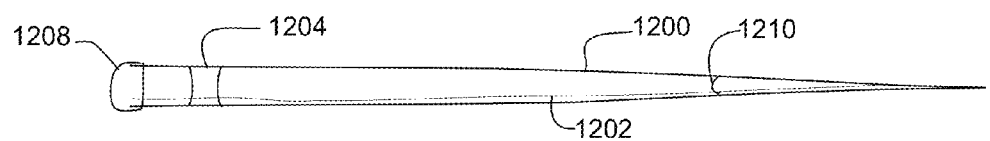

To facilitate filling of the tip of the nanocapillary, it is placed in a customized centrifuge. An example of a customized centrifuge uses a rotor from a 12 V computer fan, model FAN 3701U from StarTech. In step 1106, the centrifuge is operated, for example, at 5000 rpm for 30 minutes, which is sufficient for reproducible and reliable filling of the nanocapillary tip with fluid. FIG. 12D shows the nanocapillary after step 1106 showing the additional fluid at the tip as shown by the movement of meniscus 1210.

Figure 13:
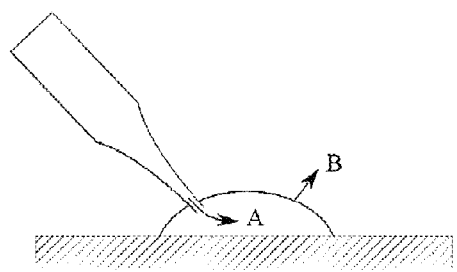
FIG. 13 shows the equilibrium between liquid flowing from the nanocapillary and liquid evaporating from the drop.

Applicants have found that the flow of the liquid can be controlled. The process of the fluid flow from the nanocapillary is a dynamic one. FIG. 13 shows the equilibrium of flow out of the nanocapillary and evaporation. The rate of fluid flow out the nanocapillary A, must be matched to the evaporation rate B, for the bubble/drop to exist. From the user's perspective the drop is stationary, but this is a misleading appearance since the situation is in fact highly dynamic. The drop is stable when the evaporation rate B matches the flow, A, from the capillary.

Figure 14:
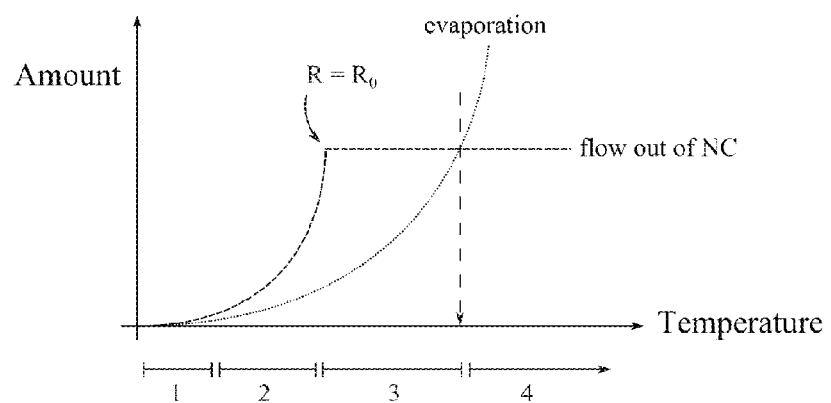
FIG. 14. shows the amount of liquid flowing from the nanocapillary and the amount of liquid evaporating from the drop as a function of temperature.
Figure 15:
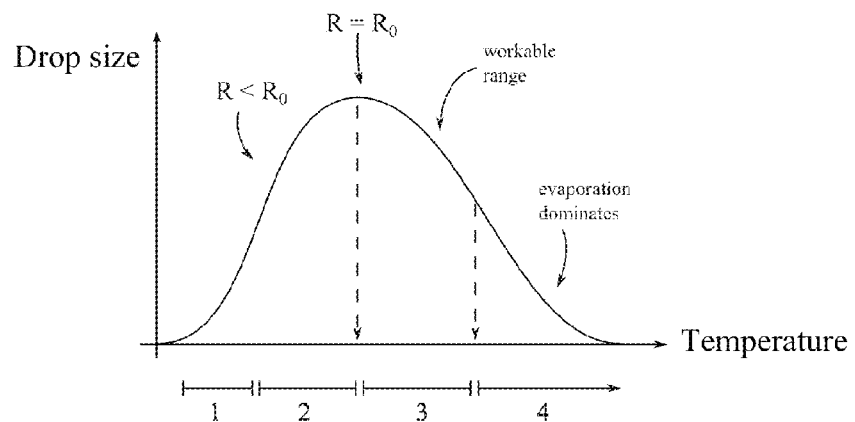
FIG. 15 shows drop size as a function of temperature.

FIG. 14 shows two curves representing A and B from FIG. 13. The evaporation rate depends on the temperature. As the temperature is increased, evaporation (B) increases. As the temperature is reduced, fluid can freeze (through evaporative cooling) at the nanocapillary tip, reducing the effective tip diameter. A reduced tip diameter reduces the amount of fluid that can flow out of the nanocapillary (A). Four regimes have been identified: (1) tip is almost fully blocked, very little flow; (2) tip is partially blocked, sub-maximal flow; (3) tip is fully unblocked, maximal flow; and (4) evaporation dominates; the user sees no bubble/drop. FIG. 15 represents the same information as FIG. 14. The effective drop size in the 4 regimes described in FIG. 14 is plotted against temperature.

Figure 16:
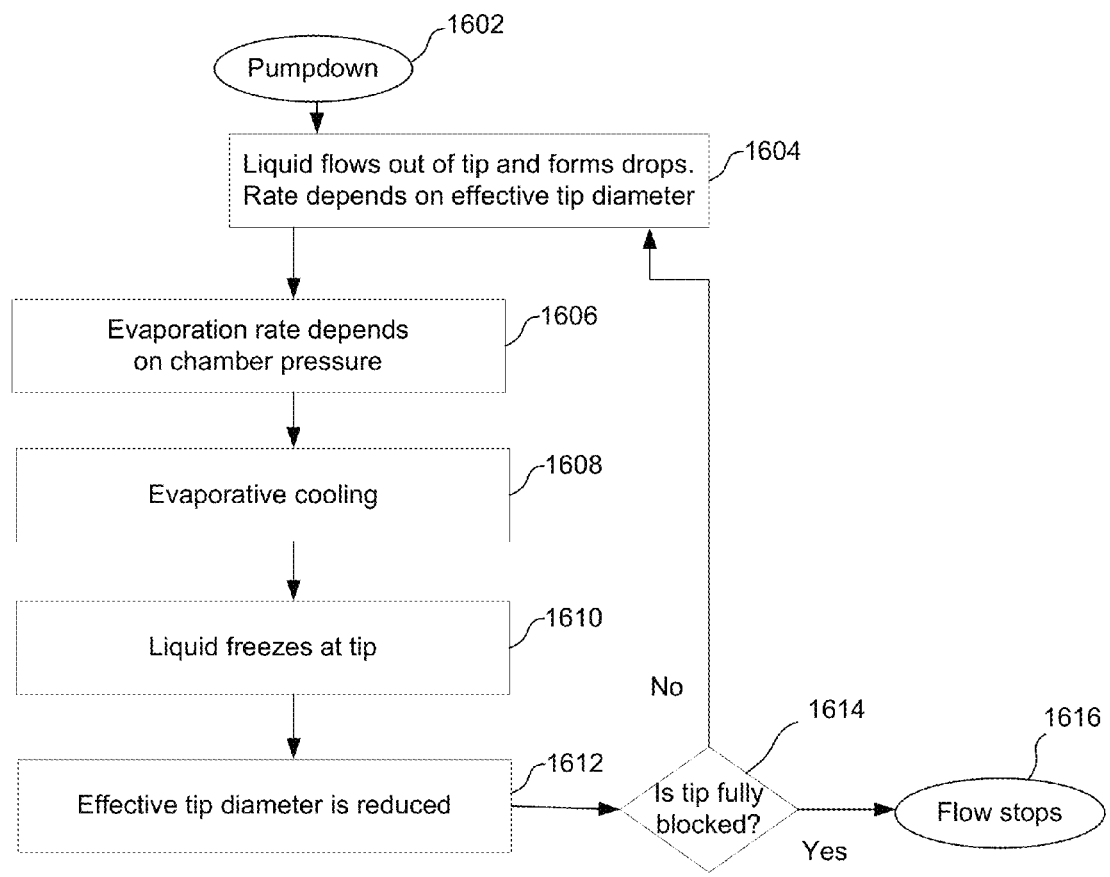
FIG. 16 shows the effects on nanocapillary flow as the pressure in the vacuum chamber is reduced.

FIG. 16 is a flowchart of occurrences during initial pump-down of chamber from atmosphere to vacuum. Conditions can be such that the nanocapillary will be sealed by freezing of the liquid as the pressure is being reduced in the vacuum chamber. If sufficient time elapses (mere minutes), the system will end up in the "flow stops" state and the nanocapillary will effectively be sealed. This seal is good enough to keep the nanocapillary ready for use for many hours after the chamber is pumped down. In block 1602, the vacuum chamber begins to be evacuated, i.e. pumped down, to operating pressure. In block 1604, liquid flows out of the tip and forms drops. The flow rate is determined by the effective tip diameter. Block 1606 shows that the evaporation rate depends on chamber pressure and can be controlled by controlling the pumpdown. Block 1608 shows that the liquid is cooled as it evaporates and block 1610 shows that the liquid freezes at the tip, reducing the effective tip diameter in block 1612. If the tip is not fully blocked, then liquid continues to flow out of the tip in block 1604. If the tip is fully blocked in decision block 1614, the flow stops as shown in block 1616. The nanocapillary can remain in that state for several hours in preparation for further processing.

Figure 17:
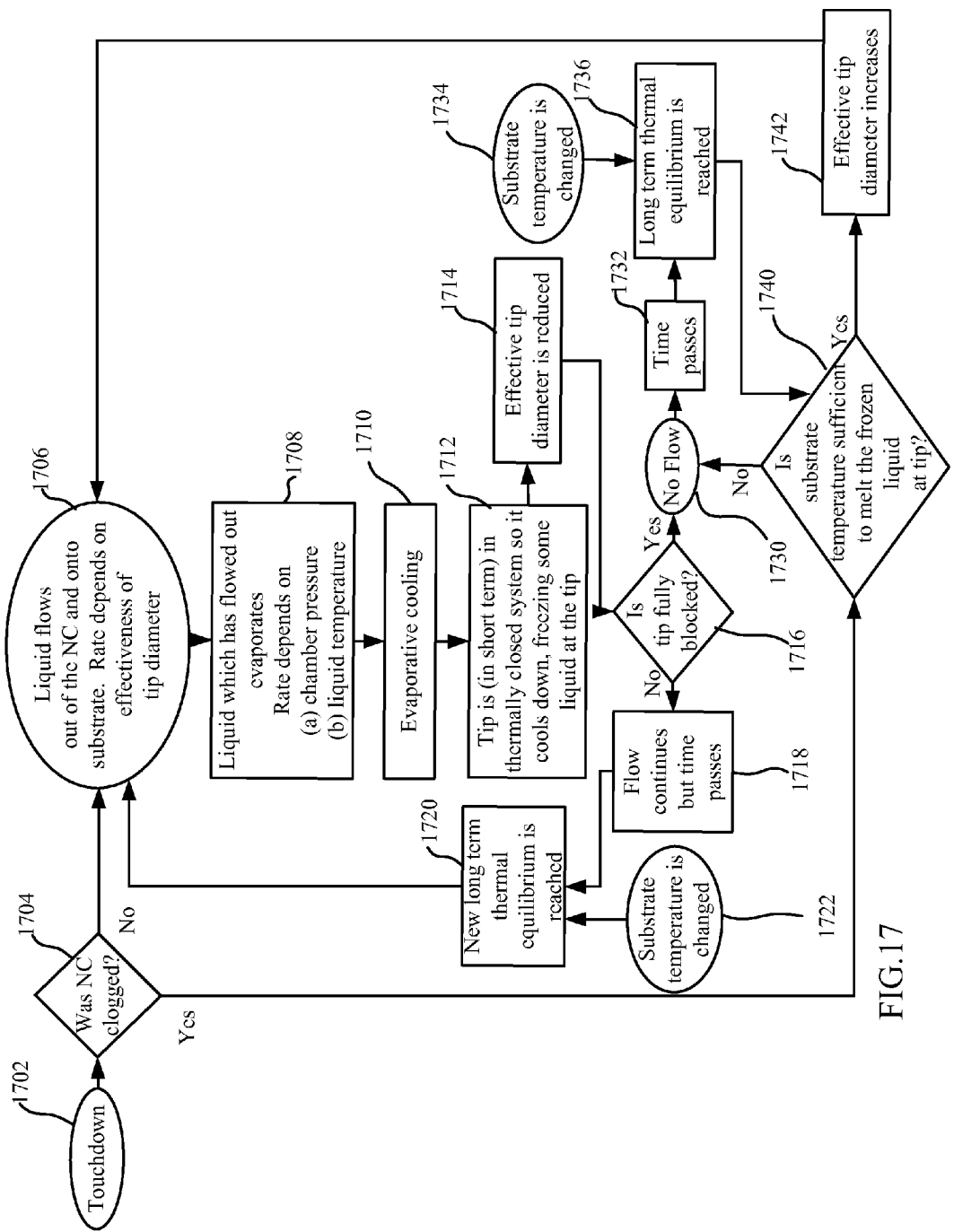
FIG. 17 shows what happens after the nanocapillary touches the work piece surface and provides a way of controlling the flow rate from the nanocapillary.

FIG. 17 is a flowchart that describes how to reach an equilibrium between the work piece temperature and the evaporative cooling of the liquid after touchdown of the nanocapillary to the substrate. The equilibrium determines the effective tip diameter, which determines the fluid flow from the nanocapillary. Thus, FIG. 17 describes a method of controlling the flow of a liquid through a nanocapillary in a vacuum chamber by controlling the chamber pressure and/or the temperature of the liquid, the work piece, or both. In High Vacuum operation mode, the vacuum chamber pressure is typically less than $10^{-4}$ mbar, more preferably less than $10^{-5}$ mbar, and most preferably less than $10^{-6}$ mbar. In Environmental operation mode, the vacuum chamber pressure typically varies between 0.1 mbar and 60 mbar, more preferably between 0.1 mbar and 20 mbar, and most preferably between 0.1 mbar and 10 mbar. The two states "flowing" and "non-flowing" are not final and given sufficient time or a change in conditions, can transition to the other state. The nanocapillary is placed in contact with the work piece in block 1702. In decision block 1704, if the nanocapillary was not clogged, then liquid flows out of the nanocapillary and onto the work piece. As described in block 1706, the flow rate depends on the effective tip diameter. In block 1708, the liquid that has flowed out of nanocapillary evaporates, depending on the chamber pressure and the liquid temperature. Block 1710 shows evaporative cooling. Block 1712 indicates that the tip can be considered, in a short time frame, a thermally closed system so it cools down and some of the liquid freezes at the tip in block 1712, effectively reducing the tip diameter in block 1714. In decision block 1716, if the tip is fully blocked, there is no flow as shown in block 1730. If not, the liquid flow continues in block 1718 and can achieve an equilibrium flow rate. If it is desired to increase the flow rate, the temperature of the work piece may be raised in block 1722 until a new long-term equilibrium is reached in block 1720, and liquid continues to flow in block 1706.

If the tip was found to be fully blocked in decision block 1716, the substrate temperature is changed in block 1734 and as time passes in block 1732, a new long-term thermal equilibrium is reached in block 1736. If the substrate temperature is sufficient to melt the frozen liquid at the tip, then the effective tip diameter has been increased in block 1742, and liquid continues to flow in block 1706. The method of FIG. 17 can be used with the nanocapillary of FIG. 10 or with any nanodispenser.

Figure 18A:
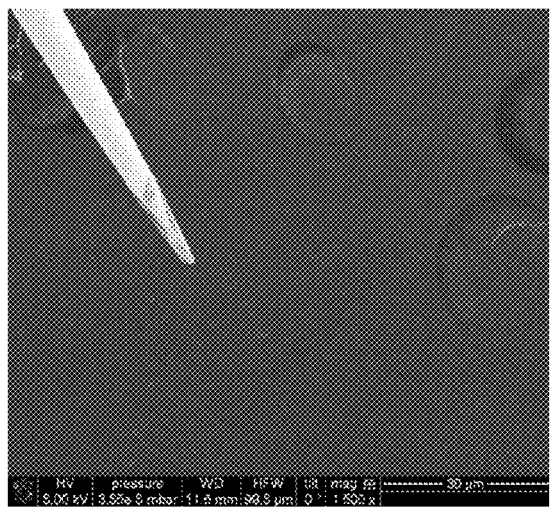
FIG. 18A-C are photomicrographs of a nanocapillary about to contact a surface (FIG. 18A), of a nanocapillary shortly after touching a surface (FIG. 18B), and of a nanocapillary after it has been in contact with the surface (FIG. 18C).
Figure 18B:
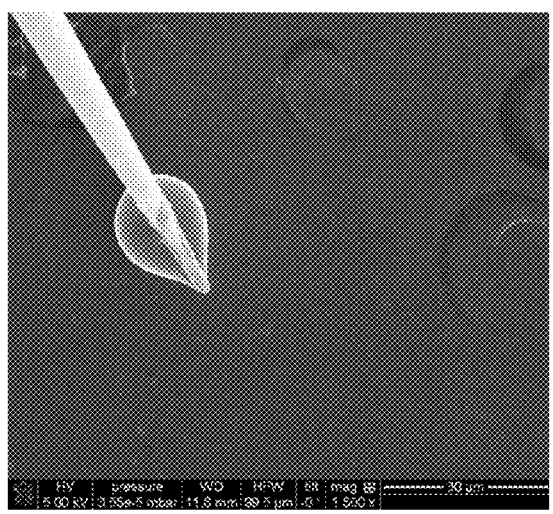
Figure 18C:
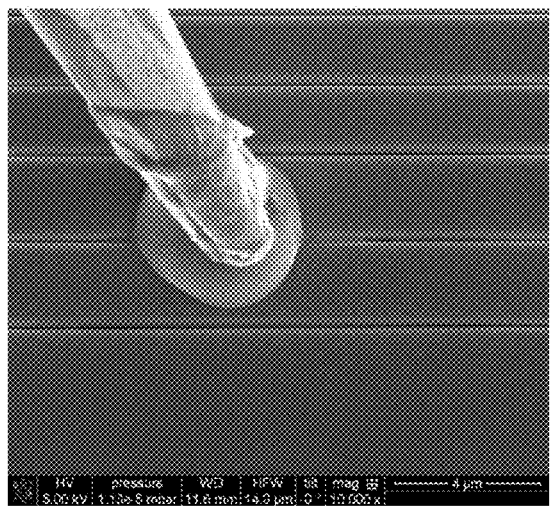

Applicants have been able to consistently produce drops smaller than 10 microns with water-based liquids. FIG. 18A shows the nanocapillary before it contacts the work piece. FIG. 18B shows the nanocapillary after touchdown with a small drop when the chamber is still in high vacuum mode. FIG. 18C shows the drop after a period of time and shows that drops can have a diameter as small as 4 microns. The liquid can form a bubble having a diameter of preferably less than 30 μm, more preferably less than 10 μm, and most preferably less than 2 μm.

Figure 19:
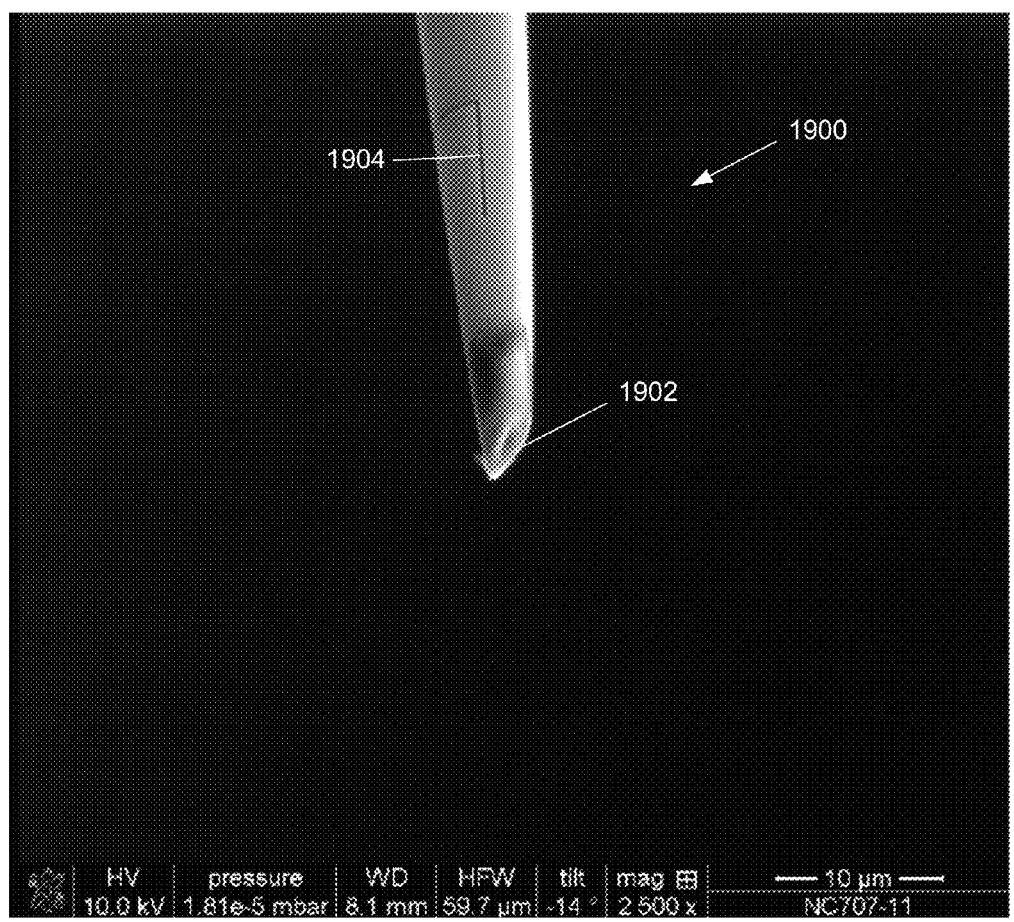
FIG. 19 is a photomicrograph of a nanocapillary that can be used in embodiments of the invention.

FIG. 19 shows another capillary 1900 that can also be used in some embodiments of the invention. The nanocapillary of FIG. 19 does not include slits near the tip. It includes an angled tip 1902 and an alignment mark 1904, as described in Botman.

Figure 20:
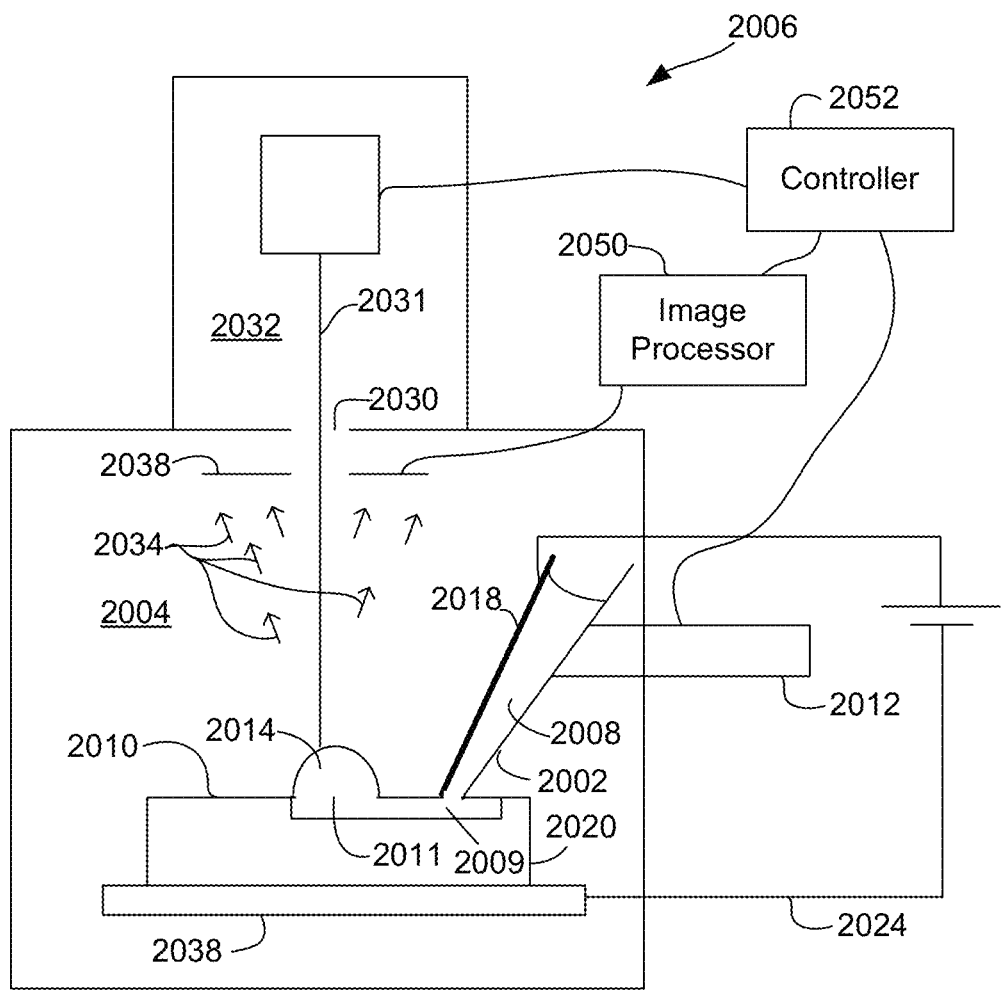
FIG. 20 shows a system in which a nanocapillary is used to provide an electrolyte for electro-deposition or electro-etching.

The nanocapillaries of the present invention can be used in any system that requires the dispensation of a small amount of liquid. For example, FIG. 20 shows a system in which a nanocapillary is used to dispense an electrolyte for electro-chemical deposition or etching.

Using an embodiment suitable for use within a charged particle beam vacuum chamber allows steps that require charged particle beam processing and steps that require electrochemical processing to be performed without repeatedly moving the work piece into and out of a vacuum chamber. Such embodiments eliminate the time consuming step of pumping down the vacuum chamber to an adequate vacuum between process steps. Also, maintaining the work piece within a vacuum chamber reduces contamination.

Multiple aspects of the invention are thought to be novel, such as the use of a channel to conduct a liquid from the point where the nanodispenser contacts the surface, the use of slits or grooves at the tip of the nanodispenser, and the control of the fluid flow as described above. For example, the nanocapillary shown in FIG. 19 and described by Botman, can be used in embodiments of the invention, as well as the nanocapillary shown in FIG. 10.

FIG. 2 describes the use of the invention with a beam-induced process. FIG. 20 shows the use of the invention for electrochemical deposition or etching.

FIG. 20 shows an embodiment of the invention in which a nanocapillary 2002 is used for electrochemical deposition or etching within sample vacuum chamber 2004 of a charged particle beam system 2006, such as an environmental scanning electron microscope. Nanocapillary 2002 is used to deliver electrolyte solution 2008 to a surface 2010. In some embodiments, a channel 2009 connects the location at which nanocapillary 2002 contacts the surface 2010 to an accumulation point that corresponds to the processing location 2011. The electrolyte flows through the channel and forms a bubble 2014 at the accumulation point, as described with respect to FIGS. 4 and 6. In other embodiments, the nanocapillary of FIG. 10 is used to deliver the electrolyte, using the method of FIG. 17 to control the fluid flow.

The surface may be hydrophilic or hydrophobic, although preferably hydrophilic. Nanocapillary 2002 is attached to a micromanipulator 2012 that preferably provides motion in three axes and rotation along the capillary axis. In some embodiments, a modified gas injection system, which is a common accessory in charged particle beam systems, can be used as the micromanipulator. One electrode for electrochemical deposition is provided by a conductive coating 2018 on, or a wire (not shown) in or on, nanocapillary 2002. The electrode associated with the nanocapillary is positively biased. In some embodiments, surface 2010 is conductive and is connected through the sample substrate 2020 or through a surface probe (not shown) to an electrode 2024 to provide a second contact for electrochemical processing. In other embodiments, the charged particle beam can function as a virtual cathode or anode, providing charges for the electrochemical reaction.

A pressure limiting aperture 2030 maintains a pressure differential between an electron optical column vacuum chamber 2032 and the sample vacuum chamber 2004 to reduce dispersion of the primary electron beam 2031 by gas molecules. Thus, evaporation of the electrolyte 2008 increases pressure in the sample vacuum chamber 2004, but much less so in the charged particle beam optical column vacuum chamber 2032. The sample in some embodiments is may be cooled or heated, for example, by a cooler or heater 2038, such as a thermoelectric cooler or heater, to modify the relative humidity at the substrate as compared to the bulk of the chamber. In some embodiments, the nanocapillary is also cooled or heated, for example, by a thermoelectric cooler or heater.

The electrochemical deposition or etching can be observed by the environmental scanning electron microscopy 2006, in which electron beam 2031 scans the region where material is being deposited and secondary electrons 2034 are emitted upon impact of electron beam 2031. The secondary electrons 2034 are amplified by gas cascade amplification and detected by an electrode 2038, forming an image whose brightness at each point corresponds to the current detected by the electrode 2038. The image can be used to monitor and adjust the progress of the electrochemical deposition or etching to provide real time feedback to an operator. The image can be used to position and guide the nanocapillary 2002 during deposition or etch.

In some embodiments, the deposition or etch can be automated. An image processor 2050 uses pattern recognition software to recognize the nanocapillary and the substrate around it. A controller 2052 controls the movement of the nanocapillary through micromanipulator 2012 in accordance with a predetermined pattern. The image from the electron microscope can provide real time position information for closed loop feedback so that the position of the nanocapillary 2002 can be controlled to produce the desired pattern on the surface 2010. The deposition or etch pattern can also be observed to adjust the deposition process, such as the speed of the nanocapillary or the pressure at which the nanocapillary contacts the surface.

As described above, the diameter of the nanodispenser is preferably sufficiently small so that the electrolyte is forced out of the nanocapillary by capillary action when the capillary is in contact with the surface, rather than through hydrostatic pressure.

The invention has multiple aspects that are separately patentable and not all aspects will be used in all embodiments.

Although the present invention and its advantages have been described in detail, it should be understood that various changes, substitutions and alterations can be made herein without departing from the spirit and scope of the invention as defined by the appended claims. The scope of the present application is not limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of dispensing liquid with a nanodispenser onto a work piece in a vacuum chamber, comprising:
   providing a nanocapillary having a diameter at the tip of less than 50~m and having at least one slit cut into the nanocapillary, the slit(s) extending to the tip; and
   contacting the tip of the nanocapillary to the work piece surface to dispense liquid from the nanocapillary onto the work piece.

2. The method of claim 1 further comprising directing a beam onto the work piece surface to initiate a reaction involving the liquid to deposit material onto the surface or to etch of material from the surface.

3. The method of claim 2 in which directing a beam onto the surface comprises directing a charged particle beam.

4. The method of claim 1 in which contacting the tip of the nanocapillary to the work piece surface to dispense liquid from the nanocapillary onto the work piece comprises contacting the tip of the nanocapillary to the work piece surface to dispense liquid from the nanocapillary onto the work piece using primarily capillary forces.

5. The method of claim 3 in which contacting the tip of the nanocapillary to the work piece surface to dispense liquid from the nanocapillary onto the work piece comprises dispensing a drop of liquid having a diameter of less than 50 µm onto the surface.

6. The method of claim 5 in which dispensing a drop of liquid having a diameter of less than 50 μm to the surface comprises dispensing a drop of liquid having a diameter of less than 10 μm.

7. A liquid nanodispenser, comprising a hollow tube for containing a liquid, the hollow tube having an inner diameter of less than 50 microns at the tip, the tip including slits that extend to the tube opening for facilitating fluid flow by capillary action from the interior of the tube to a contacted work piece surface.

8. The liquid nanodispenser of claim 7 in which the hollow tube is coated with a conductive material.

9. A method of controlling the flow of liquid from the nanodispenser of claim 1 in a vacuum, comprising:
- contacting the nanodispenser to a work piece surface in a vacuum chamber to form a bubble of liquid at the tip of the dispenser;
- adjusting the pressure in the vacuum chamber to control the rate of evaporation of the bubble; and
- adjusting the temperature of the liquid to control the rate of flow into the bubble, the equilibrium between the evaporation and the flow rate of liquid into the bubble determining the bubble size.

10. The method of claim 9 in which adjusting the temperature of the liquid comprises adjusting the temperature of the nanodispenser or the temperature of the work piece.

11. The method of claim 9 in which adjusting the temperature of the liquid comprises controlling the amount of frozen liquid at the tip by adjusting the size of the opening at the tip of the nanodispenser.

* * * * *